United States Patent
Durant et al.

(10) Patent No.: US 9,043,027 B2
(45) Date of Patent: May 26, 2015

(54) POSITIVE CONTROL OF ROBOTIC SURGICAL INSTRUMENT END EFFECTOR

(75) Inventors: Kevin Durant, Alameda, CA (US); Michael Hanuschik, Mountain View, CA (US); Paul W. Mohr, Mountain View, CA (US); Jack Hsia, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 230 days.

(21) Appl. No.: 13/483,455

(22) Filed: May 30, 2012

(65) Prior Publication Data

US 2012/0316573 A1 Dec. 13, 2012

Related U.S. Application Data

(60) Provisional application No. 61/491,647, filed on May 31, 2011.

(51) Int. Cl.
*G05B 19/04* (2006.01)
*G05B 19/18* (2006.01)
(Continued)

(52) U.S. Cl.
CPC .............. *A61B 19/2203* (2013.01); *A61B 19/56* (2013.01); *A61B 2019/4805* (2013.01);
(Continued)

(58) Field of Classification Search
CPC .................... A61B 19/2203; A61B 2019/4805; A61B 19/56; A61B 19/22; A61B 2019/26; A61B 2019/46; A61B 19/5244; A61B 2017/00026; A61B 2019/2211; A61B 2019/2223; A61B 2019/507; A61B 2019/2242; A61B 2019/2273; A61B 2019/2276; A61B 2019/2292; A61B 2019/464; A61B 2019/2234
USPC ........................................................ 700/264
See application file for complete search history.

(56) References Cited

U.S. PATENT DOCUMENTS 5,575,789 A 11/1996 Bell et al.
6,256,556 B1 * 7/2001 Zenke ........................... 700/245
(Continued)

FOREIGN PATENT DOCUMENTS

EP 2332478 A2 6/2011
WO 2006087689 A2 8/2006
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(Continued)

*Primary Examiner* — Khoi Tran
*Assistant Examiner* — Bao Long T Nguyen

(57) ABSTRACT

A method of controlling an operation of a robotically-controlled surgical instrument can include receiving a first input signal at a controller indicative of a user's readiness to actuate the surgical instrument to perform a surgical procedure, outputting an output signal from the controller to provide feedback to the user in response to the received first input signal, receiving a second input signal at the controller confirming the user's readiness to actuate the surgical instrument, outputting an actuation signal from the controller in response to receiving the second input signal, and actuating the surgical instrument to perform the surgical procedure based on the actuation signal.

28 Claims, 9 Drawing Sheets

(51) Int. Cl.
  *G05B 15/00* (2006.01)
  *G05B 19/00* (2006.01)
  *A61B 19/00* (2006.01)

(52) U.S. Cl.
  CPC .............. *Y10S 901/02* (2013.01); *Y10S 901/06* (2013.01); *Y10S 901/09* (2013.01); *Y10S 901/45* (2013.01); *Y10S 901/46* (2013.01)

(56) References Cited

U.S. PATENT DOCUMENTS

| | | | |
|---|---|---|---|
| 6,348,911 B1* | 2/2002 | Rosenberg et al. | 345/161 |
| 6,592,315 B2* | 7/2003 | Osborne, Jr. | 414/9 |
| 6,594,552 B1 | 7/2003 | Nowlin et al. | |
| 6,697,664 B2* | 2/2004 | Kienzle, III et al. | 600/427 |
| 6,817,974 B2 | 11/2004 | Cooper et al. | |
| 7,166,114 B2* | 1/2007 | Moctezuma De La Barrera et al. | 606/130 |
| 7,209,803 B2* | 4/2007 | Okamoto et al. | 700/245 |
| 7,386,365 B2 | 6/2008 | Nixon | |
| 8,226,575 B2* | 7/2012 | Levy | 600/566 |
| 2001/0034530 A1* | 10/2001 | Malackowski et al. | 606/130 |
| 2006/0095143 A1* | 5/2006 | Sunaoshi | 700/3 |
| 2006/0184279 A1* | 8/2006 | Okamoto et al. | 700/245 |
| 2008/0114494 A1 | 5/2008 | Nixon | |
| 2008/0154246 A1 | 6/2008 | Nowlin et al. | |
| 2009/0012532 A1* | 1/2009 | Quaid et al. | 606/130 |
| 2009/0088775 A1* | 4/2009 | Swarup et al. | 606/130 |
| 2010/0153317 A1* | 6/2010 | Lee | 706/12 |
| 2010/0228264 A1 | 9/2010 | Robinson et al. | |
| 2010/0256558 A1* | 10/2010 | Olson et al. | 604/95.01 |
| 2011/0087238 A1 | 4/2011 | Wang et al. | |
| 2011/0106141 A1 | 5/2011 | Nakamura | |
| 2011/0108569 A1* | 5/2011 | Jones et al. | 222/1 |
| 2011/0144806 A1* | 6/2011 | Sandhu et al. | 700/264 |
| 2011/0306986 A1* | 12/2011 | Lee et al. | 606/130 |
| 2012/0083801 A1 | 4/2012 | Nixon | |
| 2012/0109150 A1* | 5/2012 | Quaid et al. | 606/130 |
| 2012/0150154 A1 | 6/2012 | Brisson et al. | |
| 2012/0185090 A1* | 7/2012 | Sanchez et al. | 700/253 |
| 2012/0215220 A1 | 8/2012 | Manzo et al. | |
| 2012/0283745 A1 | 11/2012 | Goldberg et al. | |
| 2012/0310221 A1 | 12/2012 | Durant et al. | |
| 2012/0310254 A1 | 12/2012 | Manzo et al. | |
| 2012/0310255 A1 | 12/2012 | Brisson et al. | |
| 2012/0310256 A1 | 12/2012 | Brisson | |
| 2013/0035790 A1* | 2/2013 | Olivier et al. | 700/246 |
| 2013/0103050 A1 | 4/2013 | Richmond et al. | |

FOREIGN PATENT DOCUMENTS

| | | |
|---|---|---|
| WO | 2007034161 A2 | 3/2007 |
| WO | 2010025338 A1 | 3/2010 |
| WO | 2011125007 A1 | 10/2011 |

OTHER PUBLICATIONS

International Search Report and Written Opinion for Application No. PCT/IS2012/040034, mailed on Nov. 27, 2012, 15 pages.
International Search Report and Written Opinion for Application No. PCT/US2012/061093, mailed Feb. 25, 2013, 10 pages.
U.S. Appl. No. 61/491,698, filed on May 31, 2011.
U.S. Appl. No. 61/491,647, filed on May 31, 2011.
U.S. Appl. No. 61/491,804, filed May 31, 2011.

\* cited by examiner

POSITIVE CONTROL OF ROBOTIC SURGICAL INSTRUMENT END EFFECTOR

CROSS-REFERENCE TO RELATED APPLICATIONS

This application claims priority to U.S. Provisional Application No. 61/491,647, filed May 31, 2011, which is incorporated by reference herein in its entirety.

TECHNICAL FIELD

The present disclosure is generally directed to a safety technique for a surgical procedure. More particularly, aspects of the present disclosure relate to controlling the actuation of an end effector of a robotically-controlled surgical instrument.

INTRODUCTION

Minimally invasive surgical techniques generally attempt to perform surgical procedures while minimizing damage to healthy tissue. Robotically-controlled surgical instruments are currently used by surgeons to perform these minimally invasive procedures remotely. In such systems, surgeons manipulate input devices at a surgeon side console and a patient side console (also referred to as a patient side cart) that interfaces with a robotically-controlled surgical instrument is able to operate on a patient based on the surgeon's inputs at the surgeon side console.

Minimally invasive, robotically-controlled surgical instruments may be used in a variety of operations and have various configurations. Many such instruments include a surgical end effector mounted at a distal end of a long shaft that is configured to be inserted (e.g., laporoscopically or thoracoscopically) through an opening (e.g., body wall incision, natural orifice) to reach a remote surgical site. In some instruments, an articulating wrist mechanism is mounted to the distal end of the instrument's shaft to support the end effector and alter an orientation with reference to the shaft's longitudinal axis.

End effectors may be configured to perform various functions, including any of a variety of surgical procedures that are conventionally performed manually. Examples include, but are not limited to, cauterizing, ablating, suturing, cutting, stapling, etc. In some instances, the end effector of a robotically-controlled surgical instrument is automatically actuated once a signal is provided at the surgeon side console without the ability of the surgeon to stop the actuation once the signal is given. The remotely controlled and automatically actuated nature of robotically controlled surgical instruments can increase the risk of unintentionally actuating the end effector without the ability for a surgeon to stop the surgical procedure once actuated. Such unintentional actuation can cause the end effector to perform the surgical procedure at an undesirable location and/or at an undesirable time.

It may therefore be desirable to provide a method and system for controlling a robotically controlled surgical instrument that aids in preventing unintentional actuation of an end effector of the instrument. It also may be desirable to provide a system and method for controlling a robotically controlled surgical instrument by permitting the surgeon with sufficient time to cancel the actuation of an end effector to perform an operation that the surgeon has selected to occur.

SUMMARY

The present disclosure may solve one or more of the above-mentioned problems and/or may demonstrate one or more of the above-mentioned desirable features. Other features and/or advantages may become apparent from the description that follows.

In accordance with at least one exemplary embodiment, the present teachings contemplate a method of controlling an operation of a robotically-controlled surgical instrument. The method includes receiving a first input signal at a controller indicative of a user's readiness to actuate the surgical instrument to perform a surgical procedure, outputting an output signal from the controller to provide feedback to the user in response to the received first input signal, receiving a second input signal at the controller confirming the user's readiness to actuate the surgical instrument, outputting an actuation signal from the controller in response to receiving the second input signal, and actuating the surgical instrument to perform the surgical procedure based on the actuation signal.

In accordance with at least one exemplary embodiment, the present teachings contemplate a method of controlling an operation of a robotically-controlled surgical instrument. The method includes receiving a first input signal at an input device indicative of a user's readiness to actuate the surgical instrument to perform a surgical procedure, transmitting a first input signal in response to the first input, receiving feedback at an output device that is generated in response to the first input signal, after receiving the feedback, receiving a second input at the input device indicative of the user's readiness to operate the surgical instrument to perform the surgical procedure, and transmitting a second input signal in response to the second input to cause the surgical instrument to be actuated to perform the surgical procedure.

The present teachings also contemplate a computer-readable medium configured to cause a processor to execute the method of controlling an operation of a robotically-controlled surgical instrument.

In accordance with at least one exemplary embodiment, the present teachings contemplate a system for controlling a robotically-controlled surgical instrument, including at least one input device, at least one output device, and a controller. The at least one input device receives input from a user. The at least one output device provides feedback to the user. The controller is in signal communication with the at least one input device and the at least one output device and is configured to transmit an actuation signal to actuate at least a portion of the surgical instrument to perform a surgical procedure. The controller is configured to receive a first input signal generated in response to input at the at least one input device indicative of a user's readiness to actuate a surgical instrument and a second, subsequent input signal generated in response to input at the at least one input device indicative of the user's confirmed readiness to actuate the surgical instrument. The controller is configured to output the actuation signal after receiving the second input signal.

Additional objects and advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the invention, as claimed; rather the claims should be entitled to their full breadth of scope, including equivalents.

BRIEF DESCRIPTION OF THE DRAWINGS

The present disclosure can be understood from the following detailed description either alone or together with the accompanying drawings. The drawings are included to provide a further understanding of the present disclosure, and are incorporated in and constitute a part of this specification. The drawings, which are incorporated in and constitute a part of this specification, illustrate one or more embodiments of the present disclosure and, together with the description, serve to explain certain principles and operation. In the drawings.

DETAILED DESCRIPTION

This description and the accompanying drawings illustrate exemplary embodiments and should not be taken as limiting, with the claims defining the scope of the present disclosure, including equivalents. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or the electrosurgical instrument.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Figure 1A:
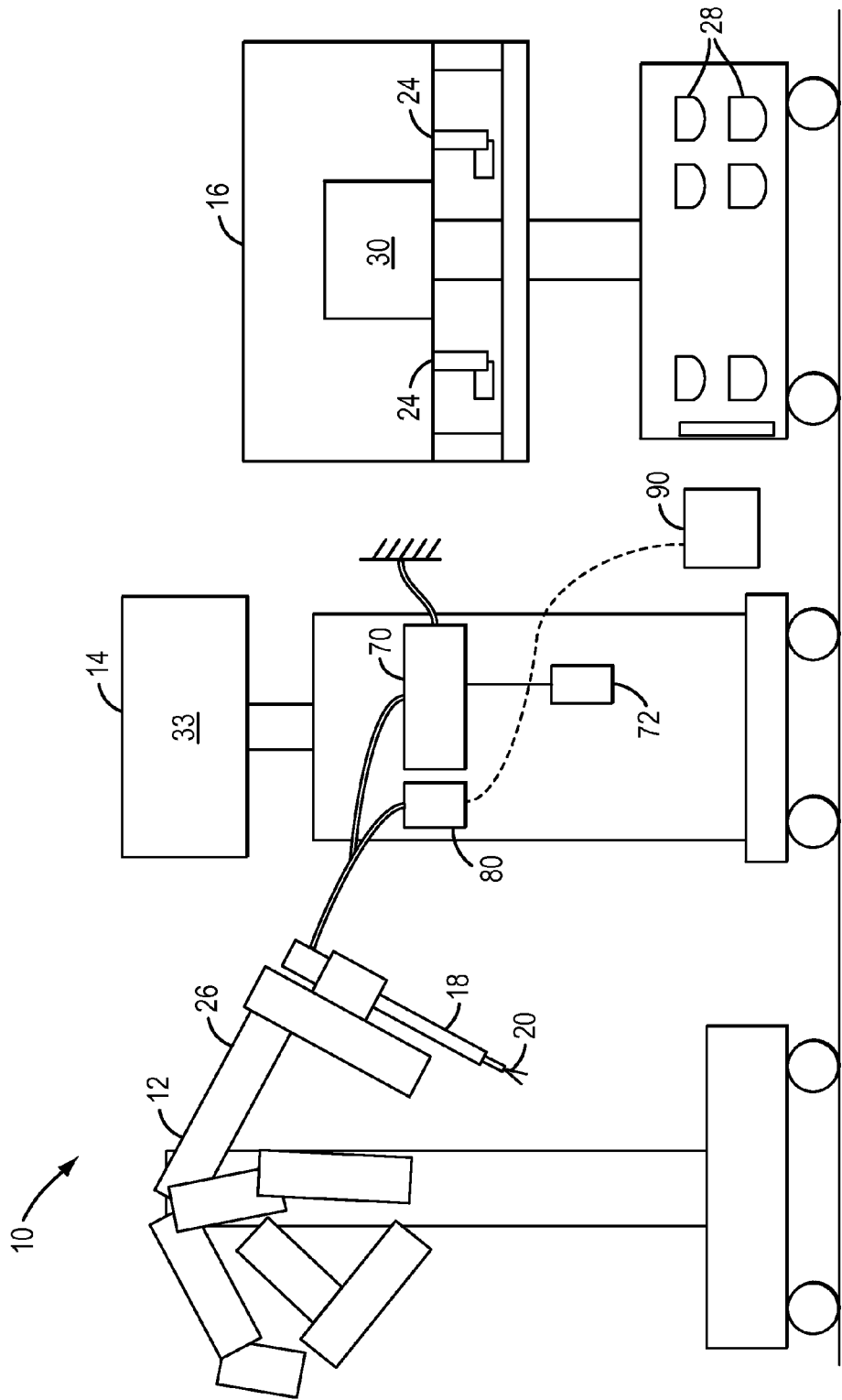
FIG. 1A is a schematic view of an exemplary robotic surgical system configured to operate a robotically-controlled surgical instrument in accordance with an exemplary embodiment.
Figure 1B:
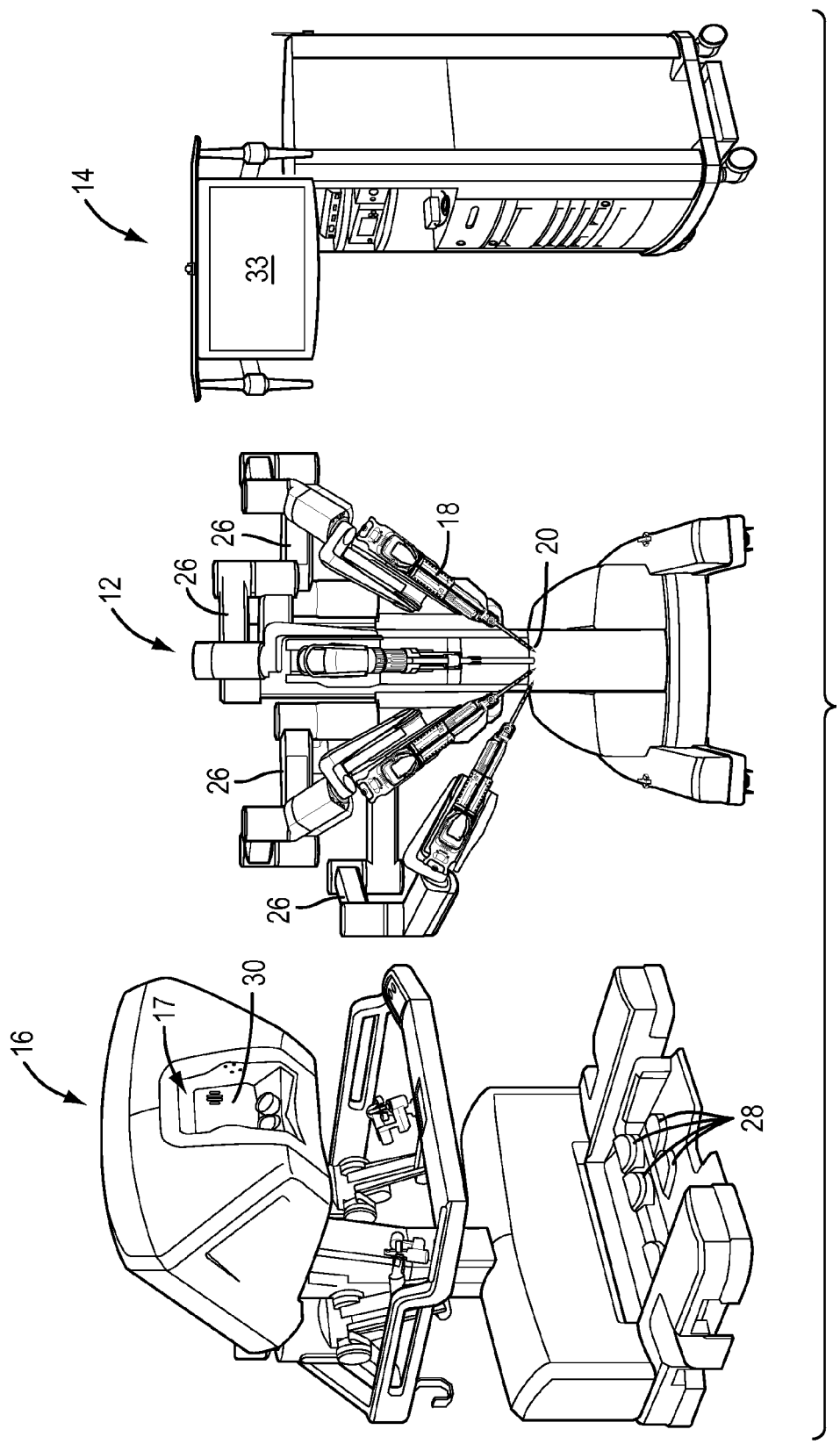
FIG. 1B is a diagrammatic view of the system of FIG. 1A.

With reference to FIGS. 1A and 1B, which are schematic and diagrammatic views, respectively, an exemplary teleoperated robotic surgical system 10 used to interface with and control a surgical instrument, such as a minimally invasive surgical instrument, in accordance with an exemplary embodiment of the present disclosure, is depicted. In an exemplary embodiment, the robotic surgical system 10 can be a da Vinci® Si (model no. IS3000) commercialized by Intuitive Surgical, Inc., but the system 10 is not so limited and can be any of a variety of robotic surgical systems. The arrangement of elements shown in FIGS. 1A and 1B is not intended to be limiting of the present disclosure and claims, but rather, as explained in more detail below, depict an exemplary surgical system with which embodiments in accordance with the present disclosure can be utilized.

The robotic surgical system 10 is used to perform minimally invasive robotic surgery by interfacing with and controlling a variety of surgical instruments, as those of ordinary skill in the art are generally familiar. The robotic surgical system 10 generally includes a patient side console 12 (also referred to as a patient side cart), an electronics/control console 14, and a surgeon side console 16, as shown in FIGS. 1A and 1B. The patient side console 12 includes various arms (also referred to as patient side manipulators) for holding and manipulating various tools. One arm is configured to interface with and control a robotically-controlled surgical instrument 18 including an end effector 20.

In general, the surgeon side console 16 receives inputs from a surgeon by various input devices, including but not limited to, gripping mechanisms 24 (e.g., controlling master tool manipulators) and foot pedals 28, etc. and serves as a master controller by which the patient side console 12 acts as a slave to implement the desired motions of the surgical instrument(s) (e.g., instrument 18) interfaced therewith, and accordingly perform desired surgical procedures. The surgeon side console 16 can also include a recessed console viewer 17 (shown in FIG. 1B) including a display 30 that allows the surgeon, when the surgeon has placed his/her head into the viewer 17, to view a three-dimensional image of the surgical site. The patient side console 12 can include a plurality of jointed arms 26 configured to hold various tools, including, but not limited to, for example, a surgical instrument with an end effector (e.g., surgical instrument 18), and an endoscope (not shown). Based on the commands input at the surgeon side console 16, the patient side console 12 can interface with a transmission mechanism of the surgical instrument to position and actuate the instrument to perform a desired medical procedure. The electronics/control console 14 receives and transmits various control signals to and from the patient side console 12 and the surgeon side console 16, and can transmit light and process images (e.g., from an endoscope at the patient side console 12) for display, such as, e.g., display 30 at the surgeon side console 16 and/or on a display 33 associated with the electronics/control console 14. Those having ordinary skill in the art are generally familiar with such robotically controlled surgical systems.

The patient side console 12 is positioned proximate to a patient and the surgical instrument 18 is used to perform various surgical procedures at a work site in the patient's body through the use of the remotely actuated end effector 20. Exemplary surgical procedures that the end effector 20 can perform include, but are not limited to, stapling, cutting, delivery of electrical energy (e.g., to cauterize and/or ablate), suturing, clamping, and combinations thereof.

In an exemplary embodiment, the electronics/control console 14 may have all control functions integrated in one or more controllers in the electronics/control console 14, or additional controllers may be provided as separate devices and supported (e.g., in shelves) on the electronics/control console 14 for convenience. The latter may be useful, for example, when retrofitting existing electronics/control consoles to control surgical instruments requiring additional functionality. Likewise, although in various exemplary embodiments, one or more input mechanisms may be integrated into an overall surgeon side platform, such as element 16 in FIGS. 1A and 1B, various other input mechanisms may be added separately and provided so as to be accessible to the surgeon during use of the system, but not necessarily integrated together in a surgeon side console 16.

Accordingly, as used herein, the term "electronics/control console" and variations thereof should be understood to include a console wherein one or more controllers (e.g., processors, such as processor 22, shown in FIG. 2) are integrated into a device that receives, processes and transmits signals to and from the patient side console 12 (and/or directly to a surgical instrument interfaced with the patient side console 12) and surgeon side console 16. In accordance with various embodiments, an electronics/control console as used herein also can include one or more separate controllers that are stand-alone devices. Further, whether as part of an integrated overall device, a separate, stand-alone device, or a combination thereof, an electronics/control console can be configured to be in direct signal communication with the surgical instrument, e.g., bypassing signal communication with the instrument through the patient side console, like processor 80, for example, in FIGS. 1A and 2. Thus, as used herein, an electronics/control console can be configured to be in signal communication through the patient side console and/or directly with the surgical instrument to control the surgical instrument. As such, a "console" does not necessarily require all controllers to be integrated into a single device and can include one or more separate control devices. Such separate controllers can be useful to add functionality to operational aspects of a surgical instrument without necessarily having to rely on servo actuators associated with the patient side console. Such controllers can also be useful when retrofitting existing robotic surgical system as a way to increase control functionality and signal processing into the electronics/control console.

One of ordinary skill in the art would recognize that the controllers, e.g., processor 22, provided at electronics/control console 14 may be implemented as part of a control system, which controls various functions of the present disclosure. One of ordinary skill in the art would recognize that functions and features of the controllers, e.g., processor 22, may be distributed over several devices or software components, including, but not limited to, processors at any of the surgeon side console 16, patient side console 12 and/or other devices, such as electrosurgical units (ESUs), incorporating processors therein. Functions and features of the control system, which may include processor 22, may be distributed across several processing devices.

A "surgeon side console" as used herein includes a console that comprises one or more input devices that a surgeon can manipulate to transmit signals, generally through the electronics/control console, to actuate a surgical instrument interfaced with a patient side console, and one or more output devices that can provide feedback to the surgeon. As used herein, it should be understood, however, that a surgeon side console can include a device that integrates the various input and output devices, with, for example, a display (e.g., substantially as shown by element 30 in FIG. 1A), but also can include separate input and/or output devices (e.g., 90 in FIG. 1A) that are in signal communication with the electronics/control console and accessible by a surgeon, although not necessarily integrated within a device with various other input devices. As an example, input devices may be provided directly at the electronics/control console and may provide input signals to a processor at the electronics/control console. As such, a "console" does not necessarily require all of the input and output devices to be integrated into a single device and can include one or more separate input and/or output devices.

Figure 2:
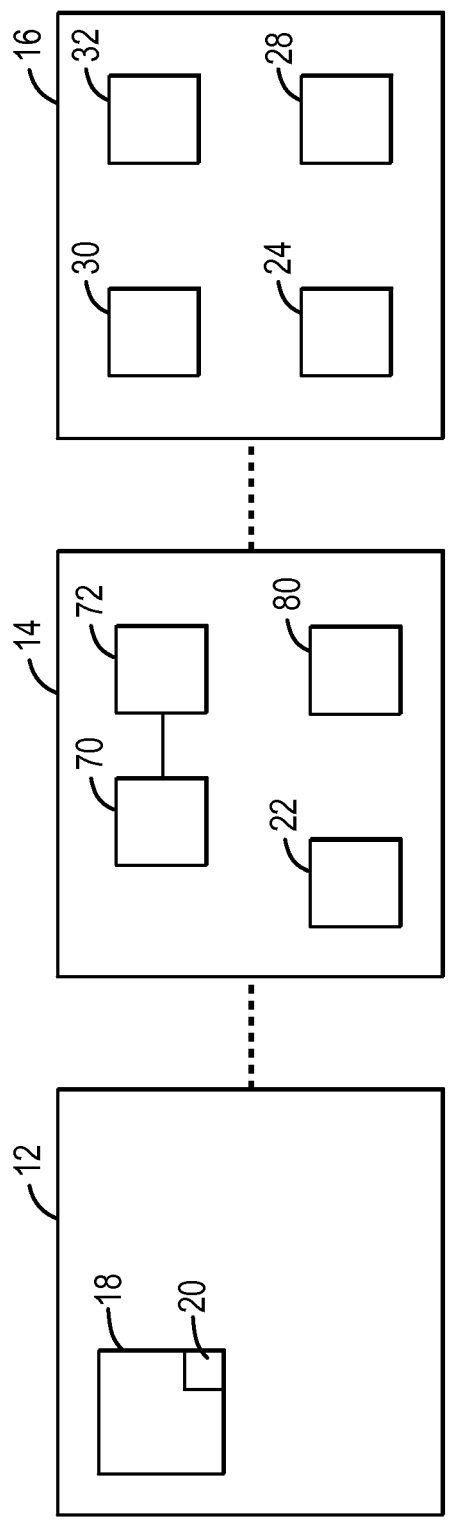
FIG. 2 is a partial schematic state diagram of the systems of FIGS. 1A and 1B according to an exemplary embodiment.

FIG. 2 is a schematic state diagram of the robotic control system showing exemplary components of a teleoperated robotic surgical system used to control the surgical instrument 18 in accordance with an exemplary embodiment of the present teachings. The electronics/control console 14 includes at least one processor 22 that controls the operation of the surgical instrument 18 and the end effector 20. In an exemplary embodiment, the processor 22 can control the operation of a cutting blade in an exemplary embodiment of the surgical instrument end effector, or alternately, another processor 80 may directly communicate with the cutting blade, bypassing signal communication with the patient side console 12.

The surgeon side console 16 may include one or more input devices 24, 28 and one or more output devices 30, 32, such as, for example, a display and a speaker. In various exemplary embodiments, suitable output devices may include, but are not limited to a display, a speaker (or other component capable of transmitting sound), and/or a component with which a surgeon is in contact that can vibrate or the like to provide haptic feedback. In various exemplary embodiments, the one or more output devices may be part of the surgeon side console 16 and signals can be transmitted from the electronics/control console 14 thereto.

As will be explained further below, the surgical instrument 18 can be in direct signal communication with the electronics/control console 14. The patient side console 12 may communicate with the electronics/control console 14, which serves as a master controller that receives and sends signals to control the surgical instrument 18, including actuation of the end effector 20 of the surgical instrument 18. The surgeon side console 16, or another input device, such as input device 90, provides input, as will be discussed in more detail below, to the electronics/control console 14, which either communicates with the patient side console 12 to control wrist articulation and joint articulation of the end effector 18 or may directly control an end effector component, such as a cutting blade, for vessel sealing, for example, or clamping and firing for a stapler. The electronics/control console 14 also is in communication with the surgeon side console 16, described in more detail below. The electronics/control console 14 includes at least one processor.

In the exemplary embodiment of FIG. 2, the electronics/control console 14 can include a processor 22 that controls one or more operational aspects of a surgical instrument through servo-actuators of the patient side console 12 with which the surgical instrument 18 transmission mechanism interfaces, and also can include a processor 80 that is in direct signal communication with the surgical instrument 18 to control one or more additional operational aspects of the surgical instrument 18. In accordance with one exemplary embodiment, for example, the surgical instrument 18 can be a fusing and cutting surgical instrument such as that disclosed in U.S. patent application Ser. No. 13/399,391, entitled "FUSING AND CUTTING SURGICAL INSTRUMENT AND RELATED METHODS," filed on Feb. 17, 2012, now published as U.S. Application Publication No. US 2012/0215220 A1 on Aug. 23, 2012, which claims the benefit of priority to U.S. Provisional Patent Application No. 61/444,400, filed on Feb. 18, 2011 and to U.S. Provisional Patent Application No. 61/491,719, filed on May 31, 2011, the disclosures of each of which are incorporated herein by reference in their entireties. In this example, a variety of operational aspects, such as, for example, gripping of the end effector, articulation of the wrist, etc. can be controlled via servo-actuators through the patient side console, while a cutting element of the end effector is controlled via a motor onboard the transmission mechanism that is configured to directly receive signals from the electronics/control console 14, for example, through a stand-alone controller (processor 80) of the electronics control console 14. One or more energy generators 70, such as, for example, electrosurgical energy generators, may be provided either separately or at the electronics/control console 14, and are configured to electrically communicate with the surgical instrument 18 to provide energy, for example, to seal tissue. An energy control module 72 controls the one or more energy generators 70 and causes the energy generator 70 to supply energy to the surgical instrument 18.

The patient side console 12 and/or surgical instrument 18 may be wired or wirelessly in communication with the electronics/control console 14. The surgeon side console 16 may be wired or wirelessly in communication with the electronics/control console 14. While the surgeon side console 16 and the electronics/control console 14 are shown in FIGS. 1A, 1B and 2 to be separately provided, the electronics/control console 14 alternately may be incorporated with the surgeon side console 16 as a single device, for example.

The surgeon side console 16 receives commands from a user, e.g., a surgeon, via manipulation of one or more input devices 24, 28 to remotely manipulate the surgical instrument 18 in order to perform a minimally invasive surgical procedure on the patient proximate to the patient side console 12. In response to the surgeon's manipulation of the one or more input devices, such as gripping mechanisms 24, input signals are transmitted to the electronics/control console 14, which in turn sends signals to control movement of the surgical instrument 18, including end effector 20, for example, by sending signals to the patient side console 12 and/or directly to the surgical instrument 18. The end effector 20 is then manipulated at the patient side console 12 to which the surgical instrument 18 is attached. However, the patient side console 12 is not limited thereto and the surgical instrument 18 may be manipulated at the patient side console 12 in any manner that provides for the operation of the surgical instrument 18.

Figure 5:
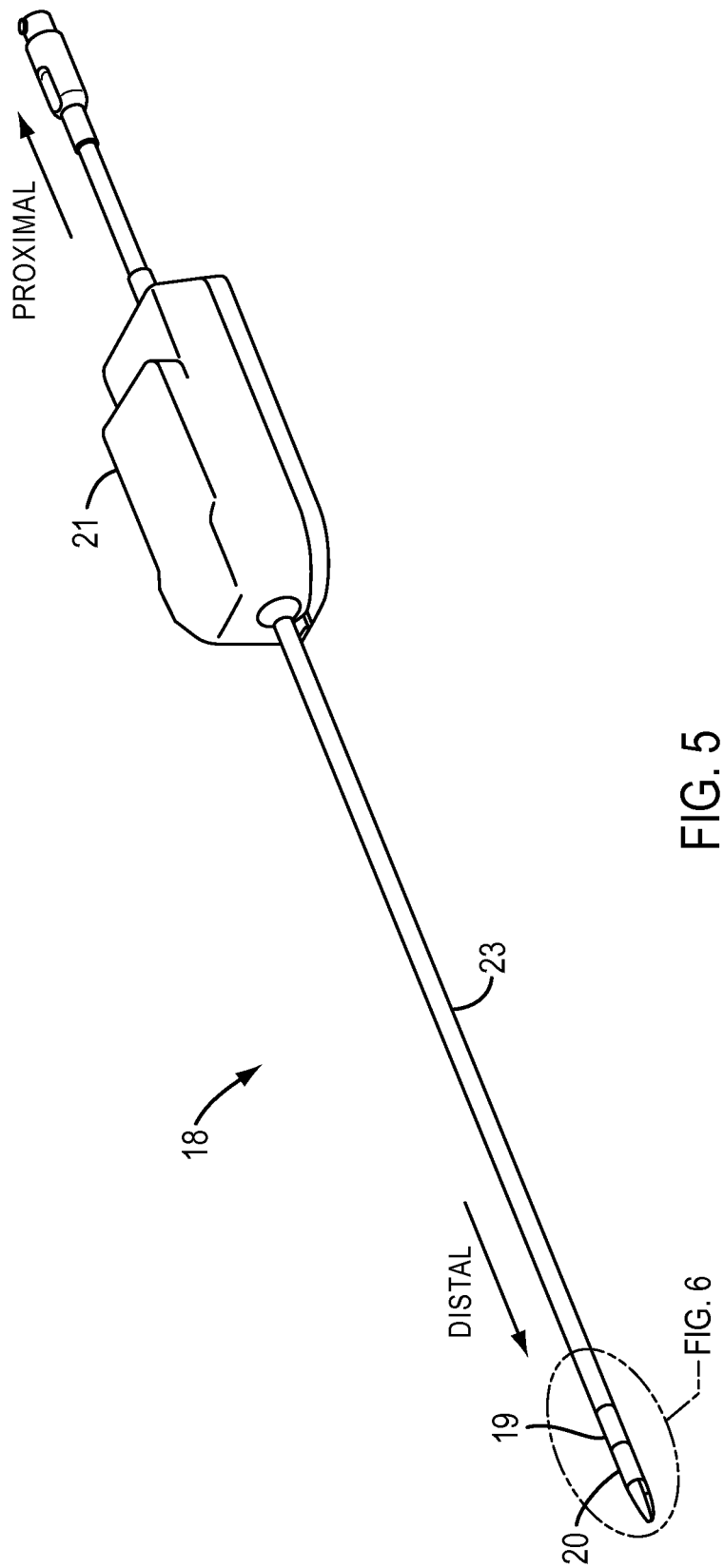
FIG. 5 is a perspective view of an exemplary embodiment of a surgical instrument configured to interface with a robotic surgical system in accordance with at least one exemplary embodiment of the present disclosure.

FIG. 5 is a perspective view of an exemplary minimally invasive surgical instrument 18. The directions "proximal" and "distal" are used herein to define the directions as shown in FIG. 5, with distal generally being in a direction further along a kinematic arm or closest to the surgical work site in the intended operational use of the instrument 18, for example, in use for performing surgical procedures. As shown in FIG. 5, the instrument 18 generally includes a force/torque drive transmission mechanism 21, an instrument shaft 23 mounted to the transmission mechanism 21, an integrated fusing and cutting end effector 20 disposed at the distal end of the instrument 18, and an articulation wrist 19 disposed at a distal end of the shaft 23 between the shaft 23 and the end effector 20.

While a wrist 19 is shown in FIG. 5, the wrist 19 is optional and the surgical instrument 18 may be used with the end effector 20 without particularly providing various degrees of freedom of the end effector 20. The end effector 20 may have various configurations and may perform a variety of operations, for example, the end effector 20 may engage in fusing only, cutting only, a combination of fusing and cutting or may operate as a stapler (which also may have a cutting blade).

As mentioned above, the transmission mechanism 21 is configured to interface with the patient side console 12, such as a manipulator arm 26 of the console 12, to receive input to drive the various motions of the instrument 18. The transmission mechanism 21 transmits received actuation inputs to resulting torques and forces to effect movement of the instrument shaft 23, wrist 19, and end effector 20, and associated components, to accomplish various motions resulting in a multi-DOF surgical instrument. For example, the transmission mechanism 21 can be controlled via torque inputs to roll shaft 23, and consequently end effector 20 (roll DOF); open and close jaws 80a, 80b (see FIG. 6B) of the end effector 20 (grip DOF); articulate wrist 19 (articulation DOF); and translate a cutting element 82 (see FIG. 6B) (translation DOF). The wrist 19 can be configured for two DOF articulation in orthogonal directions to provide both "pitch" and "yaw" movement of end effector 20 (yaw being arbitrarily defined as being the plane of motion of the end effector jaws, pitch being orthogonal to yaw).

As mentioned above, in an exemplary embodiment, the transmission mechanism 21 can be configured to receive various inputs, including, for example, torque inputs via teleoperated servo actuators of a robotic surgical system. These torque inputs can be used to transmit roll to the instrument shaft 23, to open and close the jaws 80a, 80b of the end effector 20, and to articulate the wrist 19, for example, two-DOF articulation. In addition, the transmission mechanism 21 can include an onboard electric motor (not shown) that receives input voltages, for example from a robotic surgical control system such as via an electronics/control console 14, to drive the cutting element, e.g., cutting blade 82, via gears and a rack and pinion mechanism. For further details regarding driving and controlling the cutting element 82 using an onboard motor, reference is made to U.S. patent application Ser. No. 13/483,410, entitled "SURGICAL INSTRUMENT WITH MOTOR", filed on May 30, 2012, now published as U.S. Application Pub. No. US 2012/0310254 A1 on Dec. 6, 2012, which claims priority to U.S. Provisional Patent Application No. 61/491,698, entitled "SURGICAL INSTRUMENT WITH MOTOR", filed on May 31, 2011; and to U.S. patent application Ser. No. 13/483,444, entitled "SURGICAL INSTRUMENT WITH CONTROL FOR DETECTED FAULT CONDITION," filed on May 30, 2012, now published as U.S. Application Pub. No. US 2012/0310221 A1 on Dec. 6, 2012, which claims priority to U.S. Provisional Patent Application No. 61/491,671, entitled "SURGICAL INSTRUMENT WITH CONTROL FOR DETECTED FAULT CONDITION", filed on May 31, 2011, the disclosures of each of which are incorporated by reference in their entireties.

Although the exemplary embodiment of FIG. 5 depicts a transmission mechanism 21 configured to interface and receive drive torque/force input from a robotic surgical system that includes teleoperated servo actuators, in alternative embodiments, a transmission mechanism that relies on additional onboard motors and/or manual actuation could be utilized. Persons of ordinary skill in the art will understand that depending on the number of actuation inputs available, some instrument embodiments may receive all actuation inputs from outside the instrument (e.g., from teleoperated servo motors), some (e.g., hand held instruments) may have onboard motors to drive all the instrument features, and some such as the depicted embodiment may have various combinations of external actuation inputs and onboard drive motors. In the case of onboard motors, the input voltage used to drive such motors can be supplied from a master controller (e.g., such as an electronics/control console, e.g., electronics/control console 14 as depicted in FIGS. 1A and 1B) or from voltage sources provided on the instrument itself in the case of handheld instruments.

Persons having ordinary skill in the art also will understand that various combinations of gears, pulleys, links, gimbal plates, and/or levers, etc. can be used to transmit actuating forces and torques to various instrument components. For further details regarding exemplary components that may be used in the transmission mechanism 21 to convert the inputs to the transmission mechanism 21 to torques and/or forces to ultimately drive the motions of the shaft 23, jaws of the end effector 20, and wrist 19, reference is made to U.S. patent application Ser. No. 13/484,154, entitled "GRIP FORCE CONTROL IN A ROBOTIC SURGICAL INSTRUMENT", filed on May 30, 2012, now published as U.S. Application Pub. No. US 2012/0310256 A1 on Dec. 6, 2012, which claims priority to U.S. Provisional Patent Application No. 61/491,804, entitled "GRIP FORCE CONTROL IN A ROBOTIC SURGICAL INSTRUMENT," filed on May 31, 2011; to U.S. Provisional Patent Application No. 61/491,798 and U.S. patent application Ser. No. 13/297,168, both entitled "DECOUPLING INSTRUMENT SHAFT ROLL AND END EFFECTOR ACTUATION IN A SURGICAL INSTRUMENT," filed on May 31, 2011 and Nov. 15, 2011, respectively, with U.S. patent application Ser. No. 13/297,168 being published as U.S. Application Pub. No. US 2012/0150154 A1 on Jun. 14, 2012; and to U.S. patent application Ser. No. 13/484,143, entitled "SURGICAL INSTRUMENT WITH SINGLE DRIVE INPUT FOR TWO END EFFECTOR MECHANISMS", filed on May 30, 2012, now issued as U.S. Pat. No. 8,870,912 on Oct. 28, 2014, which claims priority to U.S. Provisional Patent Application No. 61/491,821, entitled "SURGICAL INSTRUMENT WITH SINGLE DRIVE INPUT FOR TWO END EFFECTOR MECHANISMS," filed on May 31, 2011, all of which are incorporated by reference in their entireties herein. For various examples of transmission mechanisms that may be used to control tension in tendons to articulate jointed link wrist structures, reference is made to U.S. Pat. No. 6,817,974 B2, entitled "SURGICAL TOOL HAVING POSITIVELY POSITIONABLE TENDON-ACTUATED MULTI-DISK WRIST JOINT," issued Nov. 16, 2004, which is incorporated by reference herein in its entirety.

The surgical instrument 18 can be inserted (e.g., laparoscopically or thorascopically) into the body of a patient, for example, through a cannula, and advanced to a position generally in the proximity of a work site at which a cutting and fusing procedure is desired. After insertion and advancement of the surgical instrument 18 to the desired work site, the transmission mechanism 21 can receive one or more inputs to roll and/or articulate the wrist 19, such as, for example, via roll, pitch, yaw, or a combination of any of those motions. The transmission mechanism 21 can also receive inputs to translate the cutting blade 82 (shown in more detail in FIG. 6B) in proximal and distal directions. As explained above, the transmission mechanism 21 can transmit the inputs into various forces and/or torques to ultimately actuate (drive) the overall instrument shaft 23 (for example via roll) and/or to articulate the wrist 19 in pitch and/or yaw directions.

Referring again to FIGS. 1A and 1B, the surgeon side console 16 may include the plurality of input devices, for example, one or more foot pedals 28 or hand-held gripping mechanisms 24 (e.g., to control movement of the wrist 19 and instrument shaft 23). A description of the use of the foot pedals 28 is provided in more detail below. While foot pedals 28 are shown incorporated into the surgeon side console 16, it will be understood by those of ordinary skill in the art that the foot pedals 28 may be separate from the surgeon side console 16 and may be electrically connected to the electronics/control console 14. In addition, while foot pedals 28 are shown as an input device, in the alternative, additional input devices may be provided either at the surgeon side console 16 or separate from the surgeon side console 16 and connected to the electronics/control console 14. The additional input devices may be handheld devices, for example, or any other device that allows a surgeon to provide input through the input device to the electronics/control console 14 to cause the surgical instrument 18 to be manipulated. Exemplary types of input devices that can be used include, but are not limited to, buttons, mouse devices, microphones in conjunction with voice recognition software, touchscreen displays, keyboards, etc.

In various exemplary embodiments, inputs from the surgeon side console 16 can be provided to the electronics/control console 14 via the various pedals 28 (e.g., to control cutting and fusing), and via the hand-held gripping mechanisms 24 (e.g., to control movement of a wrist 19 of the instrument 18 and a shaft 23 of the instrument 18). Additional inputs may be provided via input device 90, for example, which may be provided separately from the surgeon side console 16 and the electronics/control console 14, or which may be integrated with the electronics/control console 14. Those having ordinary skill in the art are familiar with the general use of such teleoperated robotic surgical systems to provide input from a user, e.g., a surgeon, at a surgeon side console 16 to ultimately effect operation of a surgical instrument interfacing with a patient side console 12.

Figure 3:
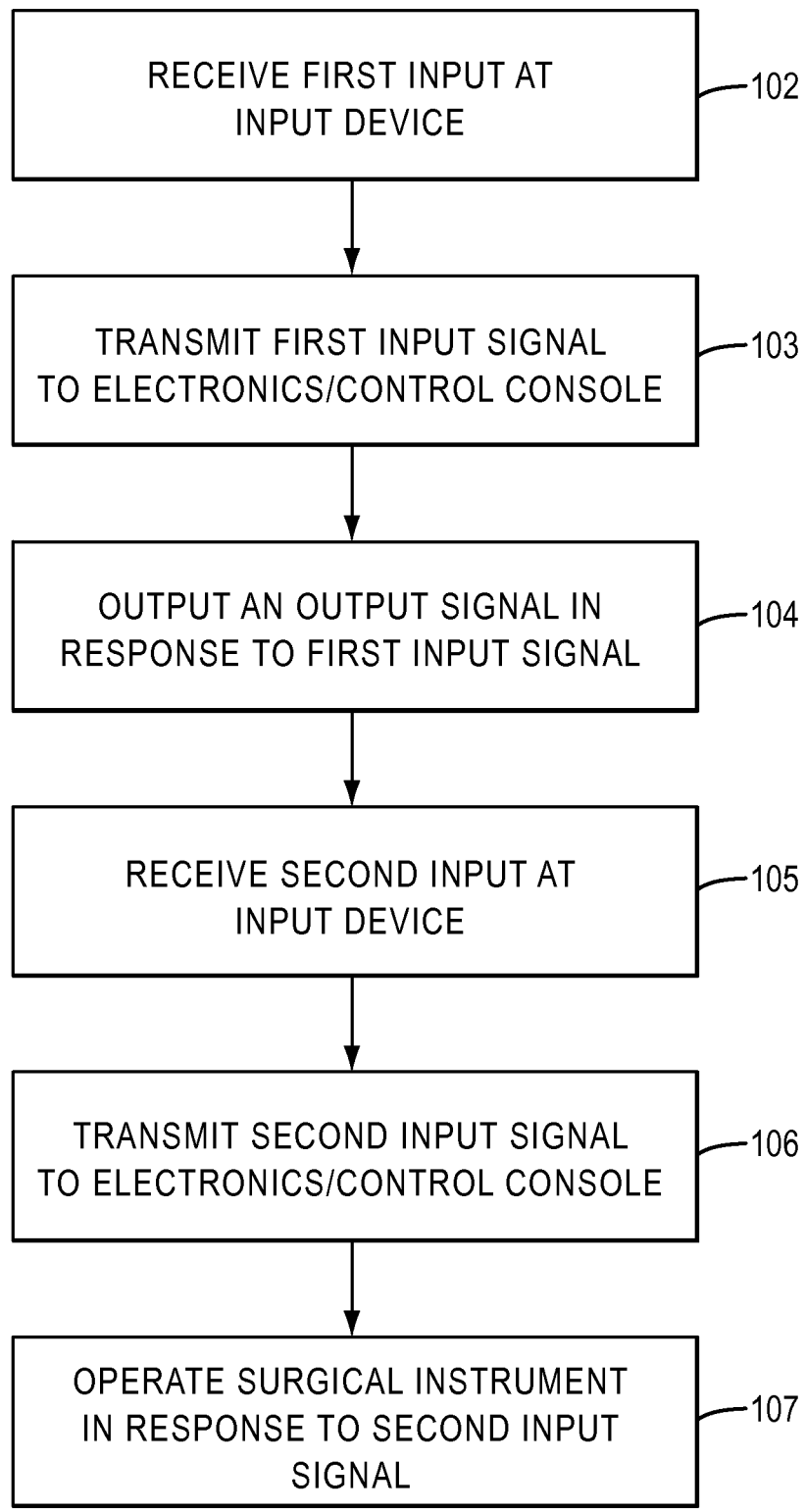
FIG. 3 is a flow diagram illustrating an exemplary method of controlling an operation of the robotically-controlled surgical instrument in accordance with at least one exemplary embodiment of the present disclosure.

FIG. 3 is a flowchart illustrating an exemplary method of controlling an operation of the robotically-controlled surgical instrument 18 that has been inserted into a patient's body (e.g., through a natural orifice or incision) with the end effector positioned and oriented (e.g., after actuation of an optional wrist mechanism or otherwise) to perform a surgical procedure at a work site in the patient's body. According to the exemplary method, at operation 102, a first input is received at an input device, such as, for example, the foot pedal 28, indicating a user's (e.g., surgeon's) readiness to actuate at least one component of the end effector 20 of the surgical instrument 18 to perform a surgical procedure. When the user determines that the end effector 20 is desired to be used to perform a surgical procedure, the user depresses the foot pedal 28 in order to "arm" the surgical instrument 18, as will be explained in more detail below. Alternatively, those ordinarily skilled in the art will appreciate that various other types of input devices can be used in lieu of or in addition to a foot pedal, including, for example, a mouse, a button, an icon or other indication on a touchscreen display, a speaker in conjunction with voice recognition software, a keyboard, etc. Moreover, as described above, the input device (e.g., such as input device 90) need not be mounted on the surgeon side console 16 shown in FIGS. 1A and 1B, but could be a handheld or other device in communication with either the surgeon's console 16 or directly with the electronics/control console 14, either via a wired communication or a wireless communication. The number and type of input devices are therefore not limited to a foot pedal. However, foot pedal 90 is shown for illustrative purposes as an input device that is separate from the input devices 28 at the surgeon side console 16, which are manipulated by the surgeon to cause other movements and/or operations of the surgical instrument 18 and/or end effector 20 to be performed.

At operation 103, an input signal resulting from input at an input device, is received at the electronics/control console 14. In response to the received input signal, indicating an armed state, the electronics/control console 14 outputs one or more output signals that result in a perceptible feedback at an output device, at operation 104. The one or more output signals can cause any of a variety of perceptible feedbacks to the user, including but not limited to visual feedback, such as for example an image, text, and/or an icon presented on a display; audio feedback (e.g., a beep, buzz, chime, click, etc., or computer-generated voice response, etc.); haptic sensation (e.g., vibration) feedback, or combinations thereof. In various exemplary embodiments, suitable output devices may include, but are not limited to be a display 30, a speaker 32 (or other component capable of transmitting sound), and/or a component with which a user, e.g., a surgeon, is in contact that can vibrate or the like to provide haptic feedback. In various exemplary embodiments, the one or more output devices, e.g., display 30, may be part of the surgeon side console 16, or may be part of the electronics/control console 14, e.g., display 33. In other exemplary embodiments, the one or more output devices can be provided proximate to the user so as to provide feedback that can be received by the user, but separately from the surgeon side console 16 and the electronics/control console 14. In the case of the feedback being an image and/or sound, such feedback may be respectively output at the display 30 and/or 33 as a visual signal and at the speaker 32 as an auditory signal.

It is to be noted that, in various exemplary embodiments, the electronics/control console 14 is provided separately from the surgeon side console 16, while in other exemplary embodiments, the electronics/control console 14 and the surgeon side console 16 may be a combined device at which the surgeon is able to remotely control the surgical instrument 18. In various exemplary embodiments, the auditory feedback may be provided to be output at the speaker 32 in concert with the visual feedback provided at the display 30 and/or 33. In other exemplary embodiments, the auditory feedback may be provided either before or after the visual feedback is output, or may be provided alone in lieu of visual feedback. It is to be noted that the present disclosure is not limited to the feedback being only visual and/or auditory output at an output device, but may be any of a variety of feedback output at an output device that are capable of being discerned by a user. For example, the feedback can be a haptic feedback signal output either alone, or in combination with one or more of the visual signal and the auditory signal.

Once a perceptible feedback is output by an output device, such as display 30 and/or speaker 32 at the surgeon side console 16, or by an output device, such as display 33 at the electronics/control console 14, the electronics/control console 14 (e.g., processor 22 and/or 80), waits to receive a second input signal resulting from a second input by the user at an input device. By way of example, the second input may include, but is not limited to, a depression of foot pedal 28 and/or input through input device 90. The second signal is transmitted to the electronics/control console 14.

In various exemplary embodiments, the user may be prompted to provide the second input. Such a prompt, for example, may be in the form of a visual image including text, and may be included as part of the feedback provided at the output device. After receiving the feedback, when the user desires to cause the end effector 20 of the surgical instrument 18 to perform the surgical procedure, in the exemplary operation of operation 105, the surgeon depresses the foot pedal 28, provides an input to input device 90, or, in other exemplary embodiments, provides any other type of second input at an input device, such as, for example, pressing a button (e.g., on a mouse or elsewhere), gripping a handheld device, speaking a command into a microphone in conjunction with voice recognition software, keystrokes on a keyboard, touching a touchscreen display, etc.

At operation 106, a second input signal provided from the second input to the input device is transmitted to the electronics/control console 14. In response to receiving the second input signal, at operation 107, the electronics/control console 14 outputs one or more actuation signals which are transmitted to cause the end effector 20 to perform the desired surgical procedure. By way of example, the electronics/control console 14 can transmit an actuation signal that causes one or more motors (not shown) (e.g., servo actuators and/or onboard motors) associated with the transmission mechanism 21 of the surgical instrument 18 at the patient side console 12 to be activated. When the one or more motors are activated, the transmission mechanism 21 transmits forces and/or torques, for example, through a system of actuation components, such as, for example, drive shafts, gears, levers, gimbal plates, rack and pinions, etc. in the transmission mechanism 21 and along the shaft 23, to operate the end effector 20 of the surgical instrument 18, at operation 107. Those of ordinary skill in the art have familiarity with various configurations of transmission mechanisms provided at the proximal end of a robotically-controlled surgical instrument 18 that are configured to interface with corresponding drive inputs provided via servo actuators on the robotic arm of the patient side console 12 to operate the surgical instrument 18. In an exemplary embodiment, the transmission mechanism 21, in addition or in lieu of receiving various inputs from servo actuators of the patient side console 12, can include one or more onboard motors (e.g., DC motors) configured to be driven by voltage that can be provided, for example, directly via the electronics/control console 14 to the onboard motor. The electronics/control console 14 can thus transmit a signal to supply voltage to such an onboard motor at the transmission mechanism 21 upon receiving the second input signal. For exemplary embodiments of surgical robotic systems that utilize a transmission mechanism of the surgical instrument that includes an onboard motor, reference is made to U.S. patent application Ser. No. 13/483,410, entitled "SURGICAL INSTRUMENT WITH MOTOR", filed on May 30, 2012, now published as U.S. Application Pub. No. US 2012/0310254 A1 on Dec. 6, 2012, which claims priority to U.S. Provisional Patent Application No. 61/491,698, entitled "SURGICAL INSTRUMENT WITH MOTOR", filed on May 31, 2011; and to U.S. patent application Ser. No. 13/483,444, entitled "SURGICAL INSTRUMENT WITH CONTROL FOR DETECTED FAULT CONDITION," filed on May 30, 2012, now published as U.S. Application Pub. No. US 2012/0310221 A1 on Dec. 6, 2012, which claims priority to U.S. Provisional Patent Application No. 61/491,671, entitled "SURGICAL INSTRUMENT WITH CONTROL FOR DETECTED FAULT CONDITION", filed on May 31, 2011, the disclosures of each of which are incorporated by reference in their entireties.

After the actuation output signal is transmitted, and the end effector 20 is operated to perform the desired surgical procedure, in an exemplary embodiment, additional perceptible feedback, such as visual, auditory, and/or haptic feedback can be output to an output device indicating that the operation of the end effector and/or surgical procedure is complete.

Figure 4A:
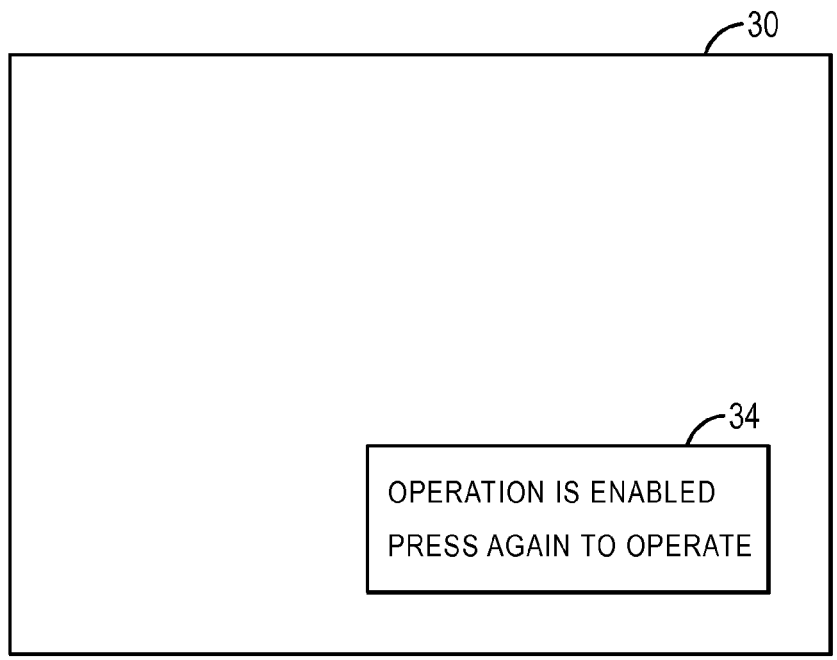
FIGS. 4A and 4B are exemplary displays used in a robotic surgical system in accordance with at least one exemplary embodiment of the present disclosure.
Figure 4B:
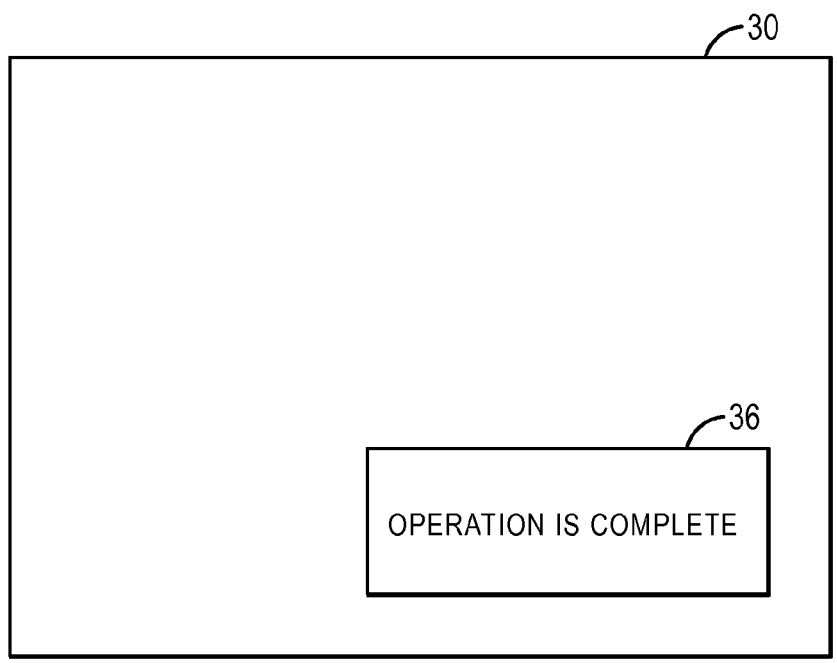

Examples of the feedback output to an output device, such as display 30 or display 33, are shown in FIGS. 4A and 4B. FIG. 4A shows a screenshot 34 of visual feedback which, in an exemplary embodiment, is provided concurrently with audio feedback at the speaker 32 in response to the first input. The screenshot 34 indicates that the operation is enabled and prompts the user to actuate the input device again to perform the operation. FIG. 4B shows a screenshot 36 of visual feedback which, in an exemplary embodiment, is provided concurrently with audio feedback at the speaker 32 in response to the second input. The screenshot 36 indicates that the operation is complete.

As will be discussed in more detail below, prior to receiving the first input at an input device indicating a user's readiness to actuate at least one component of the end effector, at operation 102, the system may determine that one or more conditions indicative of a "ready state" of the system exist, which indicate that the system is ready to perform a procedure.

Figure 6A:
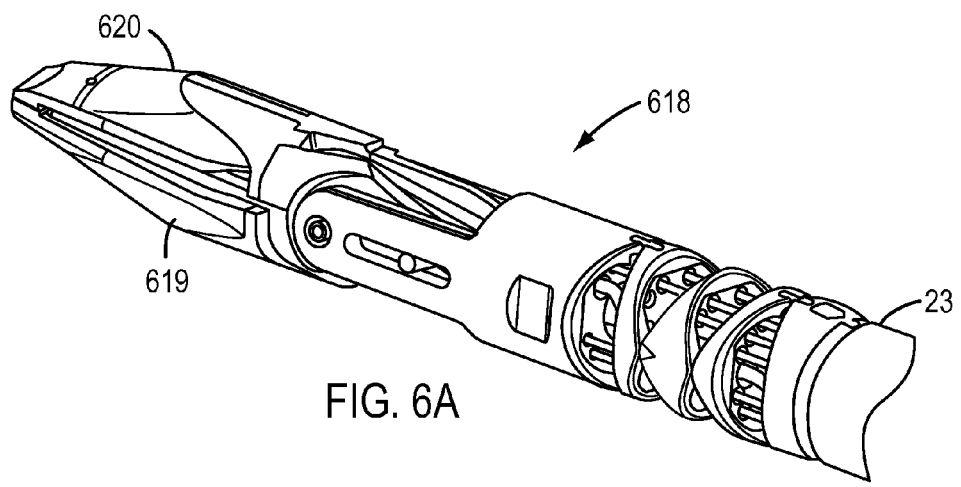
FIG. 6A is a detailed view showing an exemplary end effector and wrist at the distal end of a shaft of a surgical instrument in accordance with at least one exemplary embodiment of the present disclosure.

In an exemplary embodiment, a method and system in accordance with various exemplary embodiments of the present disclosure may be used in conjunction with a surgical instrument that is configured to perform a tissue (e.g., vessel) cutting and fusing surgical procedure. An exemplary embodiment of such a vessel seal surgical instrument is shown in the partial views of FIGS. 6A and 6B. As shown, the end effector 620 for such an instrument 618, which can be supported by an articulation wrist mechanism 619 at the distal end of the instrument shaft 23, is depicted.

As described above in relation to the inputs received by the transmission mechanism 21, the end effector 620 includes a pair of opposing jaws 80a, 80b that open and close to perform a clamping operation, a cutting element 82 disposed between the opposing jaws 80a, 80b that translates in proximal and distal directions, a wrist 619 that articulates and a shaft 23 that rolls. The jaws 80a, 80b operate to grip tissue and additionally are configured to deliver electrosurgical energy to fuse tissue together, for example, to fuse tissue of a dissected vessel in order to seal the ends of the dissected vessel. Each jaw 80a, 80b may optionally include an electrode 84a, 84b that receives energy from an associated electrical conductor. For additional details on a fusing and cutting end effector, reference is made to U.S. patent application Ser. No. 13/399,391, entitled "FUSING AND CUTTING SURGICAL INSTRUMENT AND RELATED METHODS," filed on Feb. 17, 2012, now published as U.S. Application Pub. No. US 2012/0215220 A1 on Aug. 23, 2012, which claims the benefit of priority to U.S. Provisional Patent Application No. 61/444,400, filed on Feb. 18, 2011 and to U.S. Provisional Patent Application No. 61/491,719, filed on May 31, 2011, the disclosures of each of which are incorporated herein by reference in their entireties.

Figure 6C:
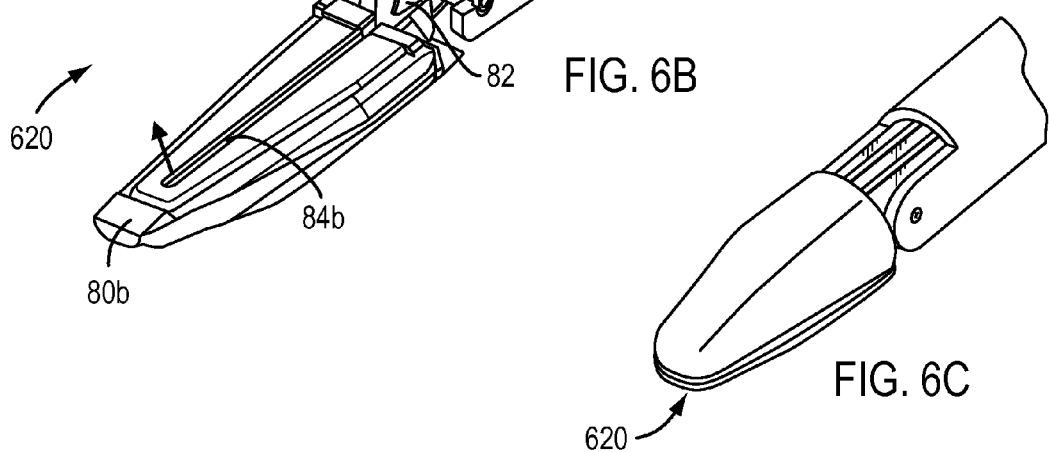
FIG. 6C is a perspective view of the end effector of FIG. 6A in a closed position.
Figure 7:
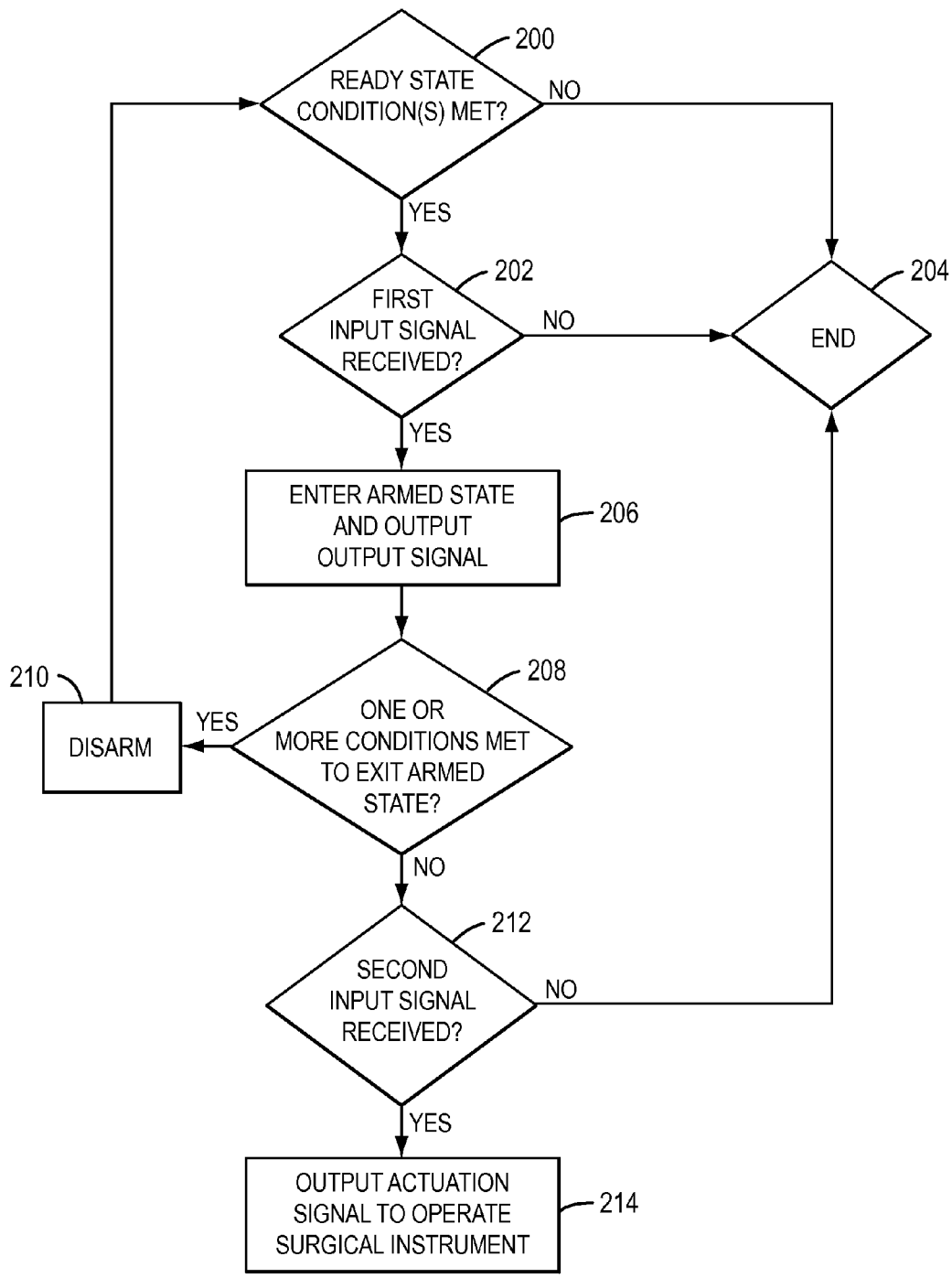
FIG. 7 is a flow diagram illustrating an exemplary method of controlling an operation of the robotically-controlled surgical instrument in accordance with at least one exemplary embodiment of the present disclosure.

FIG. 7 is a flowchart illustrating a method of controlling the operation of the end effector 620 of the robotically-controlled surgical instrument, such as surgical instrument 618, in accordance with at least one exemplary embodiment of the present disclosure. When the surgical instrument 618 is inserted (e.g., laparoscopically or thorascopically) into the body of a patient, for example, through a cannula, and advanced to a position generally in the proximity of a work site at which a cutting and fusing procedure is desired, after insertion and advancement of the surgical instrument 618 to the desired work site, the user, e.g., the surgeon, causes the jaws 80a, 80b to grip tissue desired to be cut. After the tissue is gripped, the user remotely manipulates the surgical instrument 618 through the surgeon side console 16. The surgeon may, for example, actuate input device 24, which, in an exemplary embodiment, may be a gripping mechanism, to cause the gripping mechanism to be in a gripped state. When the input device 24 is in a gripped state by the surgeon, jaws 80a, 80b of the end effector 620 are moved from the open position shown in FIG. 6A to a closed position shown in FIG. 6C in response to corresponding actuation signals transmitted by the electronics/control console 14, for example, to servo actuators of the patient side console 12, to input forces/torques to the transmission mechanism 21 at a proximal end of the surgical instrument 618 (e.g., like transmission mechanism 21 of FIG. 5).

Figure 6B:
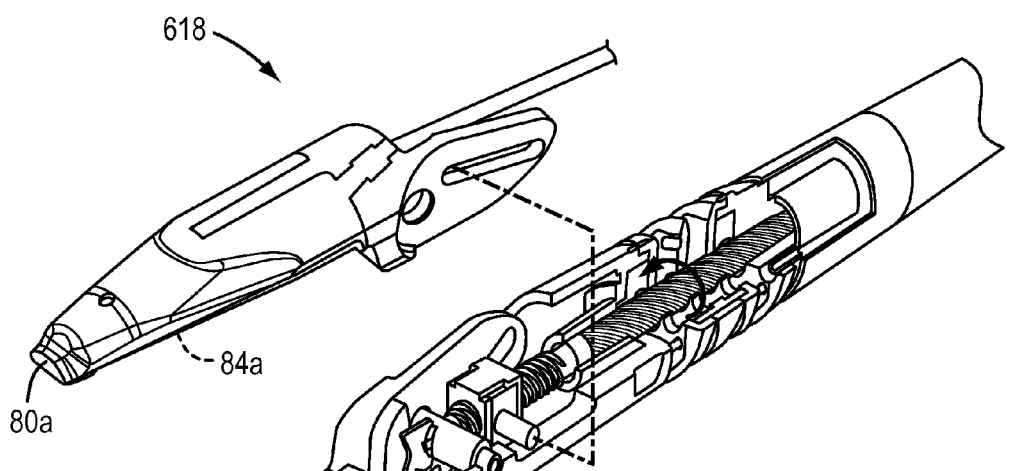
FIG. 6B is a partially exploded, partially cut-away perspective view of a portion of the surgical instrument shown in FIG. 6A in accordance with an exemplary embodiment.

At operation 200 in FIG. 7, the electronics/control console 14 determines whether one or more conditions exist that indicate a "ready state" in which the system is ready to perform a procedure using the surgical instrument, such as, for example, a cutting procedure using the surgical instrument 618. One of ordinary skill in the art would recognize that "one or more conditions" may include one, some, or all of a plurality of conditions being required to exist in order to indicate the "ready state" of the system and permit the system to transition into an "armed state." It will be understood by those of ordinary skill in the art that the term "ready state" refers to a state prior to entering an "armed state". The term "armed state" refers to a state in which the surgical instrument 618, and particularly the end effector 620, is prepared to be subsequently actuated to perform a subsequent procedure, such as a cutting procedure (i.e., jaws 80a, 80b are closed and cutting blade 82 is in a home position located proximally of the jaws 80a, 80b as shown in FIG. 6B) and is an indication at the electronics/control console 14 that a first input signal, indicating that a user is ready to actuate the cutting blade 82 to perform a cutting procedure, has been received.

The one or more exemplary conditions that indicate the "ready state" may include but are not limited to, for example, the following conditions. One condition is met when the input device, which, in an exemplary embodiment, may be a gripping input device at the surgeon side console (e.g., similar to input devices 24 shown in FIGS. 1A and 1B), has received, or is currently receiving, an initial input from the surgeon. The initial input from the surgeon may be, for example, the gripping of the input device 24 that may be a hand-controlled gripping device, which, for example, causes the jaws 80a, 80b of the end effector 620 of the surgical instrument 618 to be maintained in a nominally closed position. The initial input may be continuously received at the electronics/control console 14, indicating that the input device 24 continues to be gripped by the surgeon. In an alternative exemplary embodiment, a sensor or other indicator may be provided at the end effector 620 to indicate that, for example, the jaws 80a, 80b of the end effector 620 are in a closed position.

The system may determine that one of the conditions that indicate a "ready state" to perform a procedure is met when the arm 26 (or patient side manipulator) on which the instrument 618 is installed, which is used to perform a procedure such as a cutting procedure, is actively associated with a controlling master tool manipulator, such as one of the input devices, e.g., gripping mechanisms 24.

Another exemplary condition indicating the "ready state" is when the surgical instrument 618 is in an "in following" state. In other words, the surgical instrument 618 is "in following" when it is in a state of being actively controlled by an input device 24. In one exemplary embodiment, the "in following" state is enabled under the following conditions. Exemplary conditions for enabling the "in following" state are when the surgeon places his/her head in the recessed console viewer 17 and the surgeon selects an angle of the endoscopic camera. Another exemplary condition for enabling the "in following" state is when one or more instruments are installed on patient side manipulator(s) (e.g., instrument(s) 618 are installed on arm(s) 26) that are associated with the master tool manipulators (e.g., input devices 24). An additional exemplary condition for enabling the "in following" state is when the master tool manipulators (e.g., input devices 24) and the patient side manipulators (which have instruments installed thereon) are aligned such that the patient side manipulators are in a slave controlled state with respect to the master tool manipulators. A further exemplary condition for enabling the "in following" state is when the grip angles, which indicate the amount that the grippers are open, of the gripping devices of the master input devices 24 match the grip angles of the jaws 80a, 80b, of the surgical instrument 618 being controlled. Another exemplary condition is when there are no other ongoing conflicting activities. Examples of activities that may conflict with the surgical instrument being in an "in following" state include when a camera is being controlled, the endoscope is being aligned, and/or a master clutch is actuated, which disables the master-slave relationship between the master tool manipulators at the surgeon side console and the corresponding patient side manipulator and installed instrument.

A further exemplary condition indicating the "ready state" includes a determination that the surgical instrument 618 is electrically connected to a controlling module, such as processor 80, which controls, for example, the driving of the cutting blade 82 of the surgical instrument 618 and the subsequent cutting procedure using the cutting blade 82. For example, the controlling module, such as processor 80, may read a signal indicative of a state of a limit switch sensor in the surgical instrument 618 and may use the same signal to determine whether or not the limit switch sensor, and therefore the instrument 618, is electrically connected. For further details regarding driving and controlling the cutting element and detecting a limit switch state, reference is made to U.S. patent application Ser. No. 13/483,410, entitled "SURGICAL INSTRUMENT WITH MOTOR", filed on May 30, 2012, now published as U.S. Application Pub. No. US 2012/0310254 A1 on Dec. 6, 2012, which claims priority to U.S. Provisional Patent Application No. 61/491,698, entitled "SURGICAL INSTRUMENT WITH MOTOR", filed on May 31, 2011; to U.S. patent application Ser. No. 13/483,444, entitled "SURGICAL INSTRUMENT WITH CONTROL FOR DETECTED FAULT CONDITION," filed on May 30, 2012, now published as U.S. Application Pub. No. US 2012/0310221 A1 on Dec. 6, 2012, which claims priority to U.S. Provisional Patent Application No. 61/491,671, entitled "SURGICAL INSTRUMENT WITH CONTROL FOR DETECTED FAULT CONDITION", filed on May 31, 2011; and to U.S. patent application Ser. No. 13/399,391, entitled "FUSING AND CUTTING SURGICAL INSTRUMENT AND RELATED METHODS," filed on Feb. 17, 2012, now published as U.S. Application Pub. No. US 2012/0215220 A1 on Aug. 23, 2012, which claims the benefit of priority to U.S. Provisional Patent Application No. 61/444,400, filed on Feb. 18, 2011 and to U.S. Provisional Patent Application No. 61/491,719, filed on May 31, 2011, the disclosures of each of which are incorporated herein by reference in their entireties.

Yet another exemplary condition indicating a "ready state" includes a determination that the energy generator 70 is in communication with the energy control module 72 so that the system is enabled to provide energy from the energy generator 70 to the surgical instrument 618. In an exemplary embodiment, the system determines that the energy generator 70 is in communication with the energy control module 72 by an electronic circuit, e.g., an EPROM electronic chip, between the energy generator 70 and the energy control module 72. The electronic chip contains, for example, read only memory (ROM) which may, in an exemplary embodiment, identify the type of energy generator to which the energy control module 72 is connected. The system senses whether the electronic chip is connected or disconnected in order to determine whether the energy generator 70 is in communication with the energy control module 72. In an exemplary embodiment, the electronic chip may be provided at a cable connecting the energy generator 70 and the energy control module 72, or may be provided at a box, for example, disposed between the energy generator 70 and the energy control module.

An additional exemplary condition of the "ready state" includes a determination that no installed surgical instruments are mapped to the same input devices, e.g., one or more foot pedals 28 for controlling a cutting procedure or other procedure functionality, such as providing bipolar or monopolar energy, stapling, etc. for surgical instrument 618.

Thus, when one or more conditions indicating the "ready state" for performing the procedure are met (or, in an exemplary embodiment, all of the conditions are met), then the system may be placed in an "armed state" for performing the desired procedure, such as a cutting procedure for a vessel sealing/cutting surgical instrument such as surgical instrument 618. For example, when the electronics/control console 14 determines at operation 200 that one or more of the above-described conditions exist which are required prior to entering an "armed state", such as the input device 24 being gripped, the electronics/control console 14 thereafter determines at operation 202 whether a first input has been received at an input device, such as, for example, depression of foot pedal 28 or input at another input device like input device 90. On the other hand, when the electronics/control console 14 determines at operation 200 that one or more of the above-described conditions required to enter the "armed state" is not met, then the instrument cut state is not "armed", and the procedure ends at operation 204.

At operation 202, if a first input signal is received resulting from input by a user indicating a readiness to perform a cutting procedure via a cutting blade 82 of the end effector 620, at operation 206, the electronics/control console 14 is configured to indicate an "armed state" of the end effector 620 in response to the received first input signal at operation 202 and feedback is output to an output device, for example, display 30 or 33, and/or speaker 32. Once device feedback has been provided for output at the output device, such as, e.g., display 30, display 33, or speaker 32, then the user has been notified of the "armed state" of the surgical instrument 618. The "armed state" indicates that the user has specified a readiness to operate the surgical instrument 618 by the first input at the input device, e.g., foot pedal 28 or input device 90. The feedback may prompt the user to provide a second input indicative of the user's readiness to actuate the instrument.

The feedback output to the output device after the system transitions to the "armed state" may include one or more of the following feedback options. An "arming" sound, which may be a sound specific to the "armed state", may be output by an audio output device, such as speaker 32. The system may display a message at, e.g., display 30 or 33, indicating that the procedure, e.g., a cutting procedure, is enabled and that the user may press the input device, e.g., a foot pedal configured to initiate the cut function, again to perform the cutting procedure. The system may display a message at, e.g., display 30 or 33, indicating that the user may release the grips of the input device 24 to disable the cutting procedure. The system may display an icon at, e.g., display 30 or 33, to indicate that the system is in an "armed state" for the specific procedure. For example, the system may display a vessel-seal-armed icon.

When it is determined at operation 202 that the first input signal is not received, the procedure ends at operation 204.

In addition to providing feedback to a user indicating the "armed state" of the surgical instrument 618, when the system transitions to the "armed state", the system may, in an exemplary embodiment, fully close the grips, e.g., the jaws 80a, 80b of the end effector 620, apply a full grip torque to the jaws of the end effector 620. In addition, all axes of the arm (patient side manipulator) to which the surgical instrument 618 is installed may be locked when the system transitions into the "armed state". For an example of applying full grip torque during a procedure, reference is made to U.S. Provisional Patent Application No. 61/550,356, entitled "GRIP FORCE CONTROL FOR ROBOTIC SURGICAL INSTRUMENT END EFFECTOR", filed on Oct. 21, 2011, the disclosure of which is incorporated by reference in its entirety, to which U.S. Application Pub. No. 2013/0103050 A1, published on Apr. 25, 2012, claims the benefit of priority and also is incorporated by reference herein in its entirety.

At operation 208, after transitioning into the "armed state", the electronics/control console 14 determines whether one or more termination conditions have been met to exit the "armed state" for the surgical instrument, e.g., surgical instrument 618. In an exemplary embodiment, the system can determine whether one or more conditions for remaining in the "armed state" are no longer met. In this manner, the system can be configured such that the conditions for entering the "armed state" are stricter than those for exiting the "armed state." For example, in an exemplary embodiment, all of a plurality of conditions can be required to be met to enter the "armed state," while only one condition needs to be no longer met to exit the "armed state."

An exemplary termination condition for exiting the "armed state" includes the system determining that a fault occurs. Another exemplary termination condition includes the actuation of another input device, e.g., one of the pedals 28, that is not associated with the specific procedure to be implemented. Another termination condition for exiting the "armed state" can include an unintended movement of the patient side manipulator (e.g., arm 26 of the patient side console 12). For example, if one of the joints of the arm 26 is moved while the system is in the "armed state", which should not occur while the surgeon is actively controlling the surgical instrument, then the system will exit the "armed state". Other conditions that may result in leaving the "armed state" include, but are not limited to, for example, the surgeon removing the surgeon's head from out of the viewer 17 of the surgeon side console 16; the surgeon providing another input, such as depression of an emergency stop button; an internal fault occurring within the system; and/or control of the surgical instrument passing from one surgeon side console to another surgeon side console when there is a dual surgeon side console setup.

In addition, additional termination conditions can include any one of the requirements for entering the "armed state", i.e., any one of the conditions indicating the "ready state", being no longer met. One of ordinary skill in the art would recognize that, in an exemplary embodiment, any of the conditions indicating the "ready state" may be continuously monitored after the condition(s) were initially met and if one of the conditions indicating the "ready state" is no longer met after the system has entered the "armed state", then the system that was in the "armed state" will exit out of the "armed state."

Thus, if the user, e.g., a surgeon, determines that the user does not wish to continue with the operation of the end effector to perform the surgical procedure, the user has the option of "disarming" the operation of the end effector by, for example, releasing the input device 24, which may be a gripping mechanism. Thus, when the input device 24 is released, for example, an interruption signal, indicating that the continuous gripping of the input device 24 is interrupted, is transmitted from the input device 24 to the electronics/control console 14. The electronics/control console 14 therefore exits the "armed state" of the surgical instrument 618, and, for purposes of performing the presently-indicated operation, the surgical instrument 618 is transitioned from the "armed state" to a "disarmed state". In exemplary embodiments, the user may provide any other input with respect to the input device 24 or any of a plurality of input devices in order to transition from an "armed state" to a "disarmed state" at operation 210, which inhibits the ability to proceed with the operation of the surgical instrument 618. If the instrument enters the "disarmed state" from the "armed state", then an interruption signal may be transmitted to the electronics/control console 14 to indicate that the system has exited the "armed state".

If the user causes the operation to be disabled, then a second input signal, provided in response to the depression of the foot pedal 28 (or other input to an input device) a second time, will not result in the operation, such as a cutting operation, of the surgical instrument 618 because the "armed state" has been disabled and the surgical instrument 618 is now recognized to be in a "disarmed state". In another exemplary embodiment, an interruption signal may be transmitted to the electronics/control console 14 indicating that the "armed state" of the surgical instrument 618 should be exited after a predetermined period of time has elapsed from the output of the feedback signal at the output device, such as display 30, display 33, or speaker 32, without receiving the second input signal.

When any one of the termination conditions exist, then the electronics/control console 14 is configured to disable the "armed state" of the surgical instrument 618 and prevent the procedure, e.g., the cutting procedure, from occurring if the procedure has not yet been activated. The electronics/control console 14 can receive an interruption signal, e.g., via a processor 22 or 80, indicating that the surgical instrument is "disarmed" from the "armed" state if any of the termination conditions are satisfied. Thereafter, if the input device, e.g., one of foot pedals 28, which is configured to initiate the procedure to be performed, is actuated while any of the termination conditions exist (and the system is "disarmed"), then the system may output feedback indicating that the system will not allow the instrument to commence with the commanded procedure. For example, the system may output a sound at one of the output devices, such as an "invalid" beep, through the speaker 32, indicating that the system will not allow the instrument to commence with the procedure. The system may also output feedback at one of the displays 30, 33 indicating that the instrument is "disarmed".

If no termination conditions exist to cause the system to exit the "armed state", then the procedure determines at operation 212 whether a second input signal is received from an input device, such as, for example, foot pedal 28 or input device 90, to confirm the user's readiness to actuate the surgical instrument 618, particularly the end effector 620. As discussed above, after feedback has been output at the output device, such as display 30, display 33 and/or speaker 32, if the surgeon is ready to place the surgical instrument 618 into an operational state, a second input is input to an input device, such as foot pedal 28 or input device 90. An operational state is a state in which the end effector 620 of the surgical instrument 618, or a component of the end effector 620, such as cutting blade 82, is operated. The electronics/control console 14 determines at operation 212, whether the second input signal, transmitted as a result of the second input at an input device, is received at the electronics/control console 14. The electronics/control console 14 is configured to transition from the "armed" state to the operational state of the surgical instrument 618.

In response to receiving the second input signal, at operation 214, the electronics/control console 14 outputs an actuation signal to the surgical instrument 618 at the patient side console 12, which causes the surgical instrument 618 to operate, e.g., to cause actuation of a cutting element 82 of the surgical instrument 618. As mentioned above, the actuation signal can be transmitted to servo actuators at the patient side console 12 and/or directly to the surgical instrument 618 (e.g., to an onboard motor in the transmission mechanism). One of ordinary skill in the art would recognize that, when any one of the above-described termination conditions exist after the second input signal has been received, but before the procedure, e.g., the cutting procedure, has been activated, then the electronics/control console 14 will prevent the procedure from occurring.

The electronics/control console 14 may also output feedback to an output device, such as display 30, display 33 or speaker 32 after the operation is complete, indicating that the cutting operation has been completed.

Figure 8A:
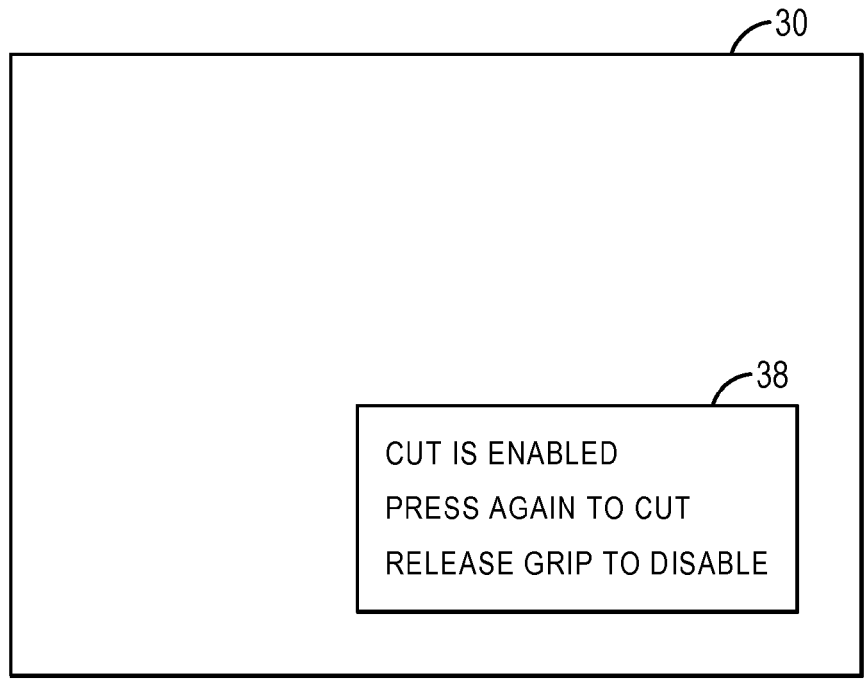
FIGS. 8A and 8B are exemplary displays used in a robotic surgical system in accordance with at least one exemplary embodiment of the present disclosure.
Figure 8B:
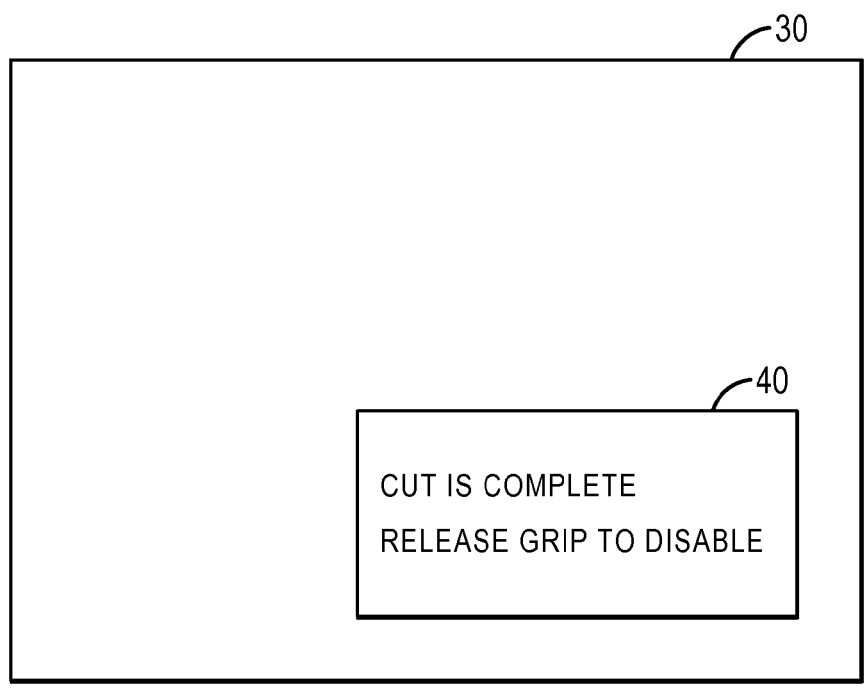

Examples of the feedback output to an output device, such as display 30 or display 33, are shown in FIGS. 8A and 8B. The first image signal that is output after the first input, such as, e.g., the depression of the foot pedal 28 or an input at the input device 90, is received may be displayed on display 30 or display 33 as a visual signal. FIG. 8A shows a screenshot 38 of visual feedback which, in an exemplary embodiment, is provided concurrently with audio feedback at the speaker 32 in response to the first input. The screenshot 38 indicates that the cutting operation is enabled or that the surgical instrument is "armed" and prompts the user to actuate the input device again to perform the cutting operation. In another exemplary embodiment, the perceptible visual feedback may be a flashing indication. The second image signal that is output after the second input, such as, e.g., the second depression of the foot pedal 28 or an input at input device 90, is received may be displayed on display 30 or display 33 as visual feedback. FIG. 8B shows a screenshot 40 of visual feedback which, in an exemplary embodiment, is provided concurrently with audio feedback at the speaker 32 in response to the second input. The screenshot 40 indicates that the cutting operation is complete.

The embodiments can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to effect the various responses and signal processing in accordance with various exemplary embodiments of the present disclosure can be implemented by a processor of or in conjunction with the electronics/control console 14, such as processor 22 or processor 80 discussed above, and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

As described above, the methods and systems in accordance with various exemplary embodiments can be used in conjunction with a surgical instrument having an end effector configured to perform multiple surgical procedures via components that are actuated via a transmission mechanism at the proximal end of the instrument. In an exemplary embodiment, as described above, the end effector may be a combined fusing, gripping and cutting end effector as shown and described, for example, in U.S. patent application Ser. No. 13/399,391, entitled "FUSING AND CUTTING SURGICAL INSTRUMENT AND RELATED METHODS," filed on Feb. 17, 2012, now published as U.S. Application Pub. No. US 2012/0215220 A1 on Aug. 23, 2012, which claims the benefit of priority to U.S. Provisional Patent Application No. 61/444,400, filed on Feb. 18, 2011 and to U.S. Provisional Patent Application No. 61/491,719, filed on May 31, 2011, the disclosures of each of which are incorporated herein by reference in their entireties. Also, in various exemplary embodiments, an end effector can include one or more components driven by one or more onboard motors disposed within the transmission mechanism itself and/or by one or more servo actuators on the patient side console configured to interface with inputs at the transmission mechanism to drive the same. For an example of using an onboard motor to drive a cutting element of an end effector, reference is made to U.S. patent application Ser. No. 13/483,410, entitled "SURGICAL INSTRUMENT WITH MOTOR", filed on May 30, 2012, now published as U.S. Application Pub. No. US 2012/0310254 A1 on Dec. 6, 2012, which claims priority to U.S. Provisional Patent Application No. 61/491,698, entitled "SURGICAL INSTRUMENT WITH MOTOR", filed on May 31, 2011; and to U.S. patent application Ser. No. 13/483,444, entitled "SURGICAL INSTRUMENT WITH CONTROL FOR DETECTED FAULT CONDITION," filed on May 30, 2012, now published as U.S. Application Pub. No. US 2012/0310221 A1 on Dec. 6, 2012, which claims priority to U.S. Provisional Patent Application No. 61/491,671, entitled "SURGICAL INSTRUMENT WITH CONTROL FOR DETECTED FAULT CONDITION", filed on May 31, 2011, the disclosures of each of which are incorporated by reference in their entireties.

Further, according to an aspect of the embodiments, any combinations of the described features, functions and/or operations can be provided.

Other embodiments of the invention will be apparent to those skilled in the art from consideration of the specification and practice of the present disclosure and claims herein. It is intended that the specification and examples be considered as exemplary only, with a true scope and spirit of the invention being indicated by the following claims.

What is claimed is:

1. A method of controlling an operation of a robotically-controlled surgical instrument, the method comprising:
receiving a first input signal at a controller, the first input signal indicating a user's readiness to actuate the surgical instrument to perform a surgical procedure;
in response to the receiving of the first input signal at the controller, outputting an output signal from the controller to provide feedback to the user, the feedback indicating the surgical instrument is in an armed state;

receiving a second input signal at the controller, the second input signal confirming the user's readiness to actuate the surgical instrument; and in response to the receiving of the second input signal at the controller, outputting an actuation signal from the controller to transition the surgical instrument from the armed state to an operational state corresponding to actuation of the surgical instrument for performance of a surgical procedure.

2. The method of claim 1, wherein the feedback is chosen from auditory, visual, and haptic feedback.

3. The method of claim 1, wherein the feedback comprises a visual output on a display and/or an auditory output from a speaker.

4. The method of claim 1, wherein the first and second input signals are generated from input by the user at an input device.

5. The method of claim 4, wherein the input device comprises a foot pedal.

6. The method of claim 5, wherein the first input signal is generated in response to a first depression of the foot pedal, and the second input signal is generated in response to a second depression of the foot pedal.

7. The method of claim 1, further comprising receiving, at the controller, a third input signal indicating that the surgical instrument is in a configuration for performing the surgical procedure and for entering the armed state.

8. The method of claim 7, wherein the third input signal is generated in response to gripping a gripping input device.

9. The method of claim 8, wherein the third input signal is received before the first input signal is received.

10. The method of claim 7, wherein one or more conditions indicate that the surgical instrument is in a configuration for performing the surgical procedure, the one or more conditions comprising at least one of:
 a first condition in which no surgical instrument other than the robotically-controlled surgical instrument is configured to map to a first input device, the first input device being configured to generate the first and second input signals in response to an actuation of the first input device, wherein the first input device is at a surgeon console of a robotic surgical system,
 a second condition in which a patient-side manipulator of a patient-side console on which the surgical instrument is installed is actively associated with a gripping input device,
 a third condition in which the surgical instrument is in a following state,
 a fourth condition in which the surgical instrument is electrically connected to a controlling module that controls one or more operations of the surgical instrument, and
 a fifth condition in which an energy generator to provide energy to the surgical instrument is electrically connected to an energy control module.

11. The method of claim 1, further comprising receiving an interruption signal at the controller, the interruption signal indicating that one or more termination conditions for leaving the armed state exists, the controller exiting the armed state in response to the receiving of the interruption signal.

12. The method of claim 11, wherein the one or more termination conditions comprise at least one of:
 an occurrence of an internal fault of a robotic surgical system controlling the robotically-controlled surgical instrument,
 movement of one or more joints of a patient-side manipulator of a patient-side console of the robotic surgical system,
 installation of another surgical instrument at the patient-side console that is mapped to a first input device configured to generate the first and second input signals,
 actuation of a second input device that is not associated with the first input device,
 release of grips of a gripping input device at a surgeon console,
 the patient-side manipulator on which the surgical instrument is installed being no longer actively associated with the gripping input device,
 the surgical instrument not being in a following state,
 the surgical instrument not being electrically connected to a controlling module that controls one or more operations of the surgical instrument, and
 an energy generator to provide energy to the surgical instrument not being electrically connected to an energy control module.

13. The method of claim 11, wherein the interruption signal is received after the first input signal is received and after the armed state of the surgical instrument is indicated.

14. The method of claim 1, further comprising exiting the armed state after a predetermined time, the predetermined time being a time from the output of the output signal during which the second input signal is not received.

15. The method of claim 1, wherein the surgical instrument comprises an end effector having jaws and a cutting element, and wherein the operational state of the surgical instrument comprises an actuation of the cutting element to perform a cutting surgical procedure.

16. The method of claim 15, further comprising receiving a third input signal at the controller before the receiving of the first input signal, wherein the third input signal is generated in response to the jaws being in a closed position.

17. The method of claim 15, further comprising receiving an interruption signal at the controller when the jaws are not in the closed position, wherein the controller transitions the surgical instrument to exit the armed state in response to the receiving of the interruption signal.

18. The method of claim 1, wherein the feedback provided to the user comprises a prompt for the user to provide an input that generates the second input signal.

19. The method of claim 18, wherein the prompt is at least one of a visual, auditory, and haptic prompt.

20. A method of controlling an operation of a robotically-controlled surgical instrument, the method comprising:
 receiving a first input at an input device, the first input indicating a user's readiness to actuate the surgical instrument to perform a surgical procedure;
 transmitting a first input signal in response to the receiving of the first input;
 receiving feedback at an output device, the feedback being generated in response to the receiving of the first input signal, the feedback indicating the surgical instrument is in an armed state;
 after the receiving of the feedback, receiving a second input at the input device, the second input confirming the user's readiness to actuate the surgical instrument to perform the surgical procedure; and
 transmitting a second input signal in response to the receiving of the second input to transition the surgical instrument from the armed state to an operational state corresponding to actuation of the surgical instrument for performance of the surgical procedure.

21. The method according to claim 20, wherein the output device is chosen from at least one of a display and a speaker, and the feedback is chosen from auditory and visual feedback.

22. The method according to claim 20, wherein the input device comprises a foot pedal.

23. The method according to claim 20, further comprising receiving, at the controller, a third signal indicating that the surgical instrument is in a configuration for performing the surgical procedure and for entering the armed state.

24. A non-transitory computer-readable medium configured to cause a processor to execute a method of controlling an operation of a robotically-controlled surgical instrument according to claim 1.

25. A system for controlling a robotically-controlled surgical instrument, the system comprising:
   at least one input device for receiving input from a user;
   at least one output device for providing feedback to the user; and
   a controller in signal communication with the at least one input device and the at least one output device, wherein the controller is configured to transmit an actuation signal to actuate at least a portion of the surgical instrument to perform a surgical procedure,
   wherein the controller is further configured to:
      receive a first signal indicating that the surgical instrument is in a ready state to enter an armed state, the armed state being a state in which the surgical instrument is ready for subsequent actuation,
      receive a second signal generated in response to input at the at least one input device, the second signal indicating a user's readiness for a surgical instrument to enter the armed state, and
      receive a third signal, subsequent to the second signal and generated in response to input at the at least one input device, the third signal indicating the user's confirmed readiness to actuate the surgical instrument, and
      wherein the controller is configured to transmit the actuation signal after receiving the third signal.

26. The system according to claim 25, wherein the third signal is received in response to the input at the at least one input device after the feedback is output to the user at the at least one output device.

27. The system according to claim 25, wherein the controller is configured to generate an output signal to provide the feedback to the user at the at least one output device in response to the received first signal.

28. A method of controlling an operation of a robotically-controlled surgical instrument, the method comprising:
   receiving a first signal at a controller, the first signal indicating that the surgical instrument is in a state ready to enter an armed state, the armed state being a state in which the surgical instrument is ready to enter a subsequent operational state corresponding to actuation of the surgical instrument for performance of a surgical procedure;
   receiving a second signal at the controller, the second signal indicating a user's readiness for the surgical instrument to enter the armed state, the second signal being generated in response to input at one or more input devices;
   outputting an arm signal from the controller in response to the receiving of the second signal at the controller, the arm signal placing the surgical instrument in the armed state;
   receiving a third signal at the controller subsequent to the receiving of the second signal, the third signal being generated in response to input at the one or more input devices, the third signal indicating the user's confirmed readiness for the surgical instrument to enter the operational state; and
   outputting an actuation signal from the controller in response to the receiving of the third signal, the actuation signal transitioning the surgical instrument to the operational state.

* * * * *